United States Patent [19]
Rogers et al.

[11] Patent Number: 6,084,121
[45] Date of Patent: Jul. 4, 2000

[54] NITRILE PROCESS

[75] Inventors: Janet Marie Rogers, Beaumont; William Randolph Leyendecker, Orange; Robert Clifford Blackstone, Beaumont, all of Tex.

[73] Assignee: E. I. du Pont de Nemours and Company, Wilmington, Del.

[21] Appl. No.: 09/392,804

[22] Filed: Sep. 9, 1999

[51] Int. Cl.$^7$ .................................................. C07C 255/00
[52] U.S. Cl. ............................................................ 558/466
[58] Field of Search .............................................. 558/466

[56] References Cited

U.S. PATENT DOCUMENTS

| | | | |
|---|---|---|---|
| 3,049,408 | 8/1962 | Gause | 23/151 |
| 3,734,943 | 5/1973 | Fitzgibbons et al. | 260/465.3 |
| 3,936,360 | 2/1976 | Wu | 203/75 |
| 4,238,295 | 12/1980 | Odom | 203/83 |
| 4,269,667 | 5/1981 | Landis | 203/76 |
| 4,981,670 | 1/1991 | Dio et al. | 423/376 |

OTHER PUBLICATIONS

Masahiro Kurabayashi et al, Destabilization of Liquid Hydrogen and Stabilizer, Kogyo Kagaku Zasshi 71(7), 984–989 (1968?).

*Primary Examiner*—Johann Richter
*Assistant Examiner*—Joseph Murray

[57] ABSTRACT

A process for purifying a nitrile such as acrylonitrile is disclosed. The process comprises (1) contacting a product mixture, which comprises acrylonitrile and hydrogen cyanide, with glycolic acid or a glycolic acid-generating compound to produce a glycolic acid-treated product; and (2) recovering the nitrile from the glycolic acid-treated product. The product mixture can be produced by contacting ammonia with an olefin under a condition effective to produce a nitrile and hydrogen cyanide.

19 Claims, No Drawings

NITRILE PROCESS

FIELD OF THE INVENTION

The present invention relates to a process for recovering or purifying a nitrile from a mixture comprising the nitrile and hydrogen cyanide and to a process for producing a nitrile, especially acrylonitrile, from an olefin and ammonia.

BACKGROUND OF THE INVENTION

A nitrile such as acrylonitrile or its derivative such as methacrylonitrile, is an important industrial chemical, especially in the plastics, surface coatings, and adhesive industries. For example, acrylonitrile can be used to produce acrylic fiber, as intermediate in the synthesis of antioxidants, pharmaceuticals, dyes, and surface active agents. It can also be used as a modifier for natural polymers or as a pesticide fumigant agent for stored grain.

The production of acrylonitrile or its derivative by the catalytic ammoxidation of an olefin is well known and widely used. For example, the olefin used for producing acrylonitrile is propylene or propane. In this process, the olefin, ammonia and air are reacted over a catalyst at an elevated temperature, producing a vaporous mixture of acrylonitrile, acetonitrile, and hydrogen cyanide, along with water and other side-reaction products. The hot vapor is then cooled and quenched with sulfuric acid to remove unreacted ammonia. The vapor stream is then sent to a recovery system. It is first absorbed in water to create an aqueous stream containing the products of the reaction: acrylonitrile, acetonitrile, and hydrogen cyanide. The aqueous stream is then treated in a series of distillation columns to recover and purify these products. After the acetonitrile is removed for recovery, the hydrogen cyanide is stripped from the acrylonitrile stream, sent to a purification column, and chilled for storage.

Acetic acid is generally introduced during the separation of hydrogen cyanide from acrylonitrile. However, the use of acetic acid in the process has some disadvantages. Some of the acetic acid remains with the acrylonitrile stream, causing corrosion of metal equipment, and potentially remaining as an impurity in the acrylonitrile. In addition, it reacts with residual ammonia to form ammonium acetate, which is then carried by recycle streams back to the first part of the recovery and purification systems where it tends to decompose or release harmful ammonia to the process.

Stronger mineral acids such as phosphoric and sulfuric acids are also often used in processes for the direct production of hydrogen cyanide from methane or methanol as the carbon source. Since these processes produce few or little recoverable byproducts, the mineral acids do not affect the system adversely. However, mineral acids cannot be used in processes where acrylonitrile is the main product because they can react with acrylonitrile, especially under anhydrous conditions such as are found in acrylonitrile purification processes.

Therefore, there is an increasing need to develop a process for the purification of a nitrile such as, for example, acrylonitrile.

SUMMARY OF THE INVENTION

This invention comprises (1) contacting a product mixture, which comprises a nitrile and hydrogen cyanide, with glycolic acid or a glycolic acid-generating compound to produce a glycolic acid-treated product; and (2) recovering the nitrile from the glycolic acid-treated product.

DETAILED DESCRIPTION OF THE INVENTION

According to the invention, the product mixture can be obtained from any source as long as the product mixture comprises a nitrile and hydrogen cyanide. Presently it is preferred that the product mixture be produced by a process which comprises contacting an olefin with ammonia and air to produce a product mixture comprising a nitrile and hydrogen cyanide.

The product mixture, which comprises a nitrile and hydrogen cyanide, is generally contacted with glycolic acid or glycolic acid generating compound to produced a glycolic acid-treated product. According to the invention, the product mixture can be contacted with glycolic acid during the recovery or purification of the nitrile. Examples of suitable glycolic acid-generating compounds include, but are not limited to, esters of glycolic acid, monochloroacetic acid, oxalic acid, and combinations of two or more thereof.

The amount of glycolic acid or glycolic acid-generating compound used can be any quantity so long as the amount can substantially prevent the polymerization thereby facilitating the recovery or purification of the nitrile such as acrylonitrile. Generally, the molar ratio of glycolic acid to hydrogen cyanide present in the product mixture can be in the range of from about 0.001:1 to about 1000:1. Alternatively, the amount of glycolic acid or glycolic acid-generating compound is the amount that can lower the pH of the product mixture to about 4.2 or lower. The contacting can generally be carried out at a temperature in the range of from about 25° C. to about 130° C., preferably about 30° C. to about 100° C., under a pressure that can accommodate the temperature range, and for a time sufficient to separate, recover, or purify the nitrile, generally about 10 seconds to about 2 hours.

According to the invention, the term "nitrile" refers to a compound having the formula of RCN in which R is a hydrocarbyl radical having 1 to about 10 carbon atoms per radical. The presently preferred nitrites are acrylonitrile, methacrylonitrile, or combinations thereof. The olefin can be ethylene, propylene, isobutylene, butene, pentene, propane, or combinations thereof. The presently preferred olefin is propylene because acrylonitrile can be produced from propylene.

The contacting of olefin with ammonia and air is generally carried out in the gas phase in a suitable vessel such as, for example, a fluidized bed reactor having an air compressor and a quench column. An olefin such as, for example, propylene and ammonia can be vaporized and introduced into the vessel or reactor. The molar ratio of olefin to ammonia can be any ratio so long as a nitrile can be produced. Generally, the molar ratio can be in the range of from about 0.1:1 to about 10:1, preferably about 0.2:1 to about 5:1, and most preferably about 0.5:1 to about 2:1. The contacting can be carried out under any suitable condition such as a temperature in the range of from about 250 to about 600, preferably about 300 to about 550, and most preferably about 350 to about 500° C., under a pressure that can accommodate the temperature range, and for a time sufficient to produce a nitrile, generally about 10 seconds to about 2 hours.

The contacting of olefin with ammonia and air can also be carried out in the presence of an ammoxidation catalyst, as disclosed in U.S. Pat. Nos. 3,936,360 and 4,981,670, the disclosures of which are incorporated herein by reference. Because an ammoxidation catalyst is well known to one skilled in the art, the disclosure of which is omitted herein for the interest of brevity. The contacting produces a product mixture comprising a nitrile and hydrogen cyanide, generally in gas or vapor phase.

Generally, a product mixture produced any source is cooled to a temperature in the range of from about 200 to about 270° C. to produce a cooled product mixture. The cooled product mixture is then quenched, with a quenching solution that comprises water and a recycled stream as defined in U.S. Pat. No. 3,936,360, to about 30 to about 90° C. to produce a quenched mixture. The quenched mixture is then contacted with sulfuiric acid at about 70 to about 90° C. The amount of sulfuric acid can be any amount as long as it is sufficient to react any excess or ammonia to produce a quenched product.

The spent quenching solution can be generally further treated such that high-boiling materials, primarily catalyst fines, tars and other organic materials are concentrated, cooled, and routed to waste treatment along with the water generated by the contacting of olefin and ammonia.

Generally, the product mixture vapor can be routed to an absorber in which the organic materials are absorbed in chilled water. Nitrile and hydrogen cyanide, in the aqueous stream from the absorber containing the dissolved organic materials, are separated from the bulk of the water. Generally the separation can be carried out by azeotropic-extractive distillation, using water as the solvent. If the olefin is propylene, acetonitrile is generally also present in the product mixture and can be separated from acrylonitrile and hydrogen cyanide. The acrylonitrile and hydrogen cyanide are removed via the overhead stream and can be further purified. Acetonitrile and other organic materials are separated from the water in the bottom stream, which contains water and acetonitrile. The water can be recycled to serve as the solvent in both the absorber and the recovery of nitrile.

The product mixture can be further purified by any means known to one skilled in the art such as that disclosed in U.S. Pat. No. 3,936,360. Because the purification is well known, the description of which is omitted herein.

EXAMPLES

The following examples are intended to illustrate the invention but are not to be interpreted to unduly limit its scope.

Example 1

A 400 ml sample of crude acrylonitrile from the drying column of a DuPont plant in Beaumont, Tex. was treated with 1 ml of glycolic acid and then distilled down to a volume of 75 ml, simulating a distillation as carried out in most acrylonitrile processes. No tendency to react, polymerize, or form additional color was noted. A control sample, using acetic acid, had a darker color. Gas chromatography of the distillates showed no change in composition or impurities in the two samples.

This example illustrates that glycolic acid was a more effective processing aid than acetic acid during the distillation of crude acrylonitrile, enabling the use of smaller quantities.

Example 2

A 200 ml test sample of an acrylonitrile plant stripper overhead stream, containing acetonitrile, acrylonitrile, water, about 2% hydrogen cyanide, and traces of ammonia, was treated with 0.5% by weight of glycolic acid. A control sample of the same stream was treated with 0.5% acetic acid. The test sample darkened less rapidly than the control sample.

This example further demonstrates that glycolic acid was a more effective processing aid than acetic acid for the acrylonitrile stripper overhead.

Example 3

The partition coefficients of glycolic acid and acetic acid between water and acrylonitrile were determined by stirring 100 ml each of acrylonitrile and water with 100 $\mu$l of each acid followed by titration to a pH of 8.2 of 5 ml aliquots of each layer. The partition ratio of glycolic acid was 21.4 in favor of water, whereas the partition ratio of acetic acid was 2.31.

This example illustrates that, unexpectedly, much less of glycolic acid than acetic acid remained in the organic phase. On the other hand, acetic acid partitioned into both phases. The organic phase generally passes on to the product recovery equipment causing corrosion. Because glycolic acid partitioned almost entirely into the water phase, corrosion of equipment would be substantially reduced.

Example 4

The relative effectiveness of glycolic acid and acetic acid in lowering the pH of an ammonia-buffered solution was tested. An aliquot (5 ml; 79 mmoles) of concentrated ammonium hydroxide was added to each of two 300 ml samples of water to give a pH above 11. Then each was titrated to a pH of 4.2 with each acid. It required 16 ml of 100% acetic acid (280 mmoles), but only 8.9 ml of 70% glycolic acid (103 mmoles) to reach the given pH.

This example illustrates that a much smaller amount of glycolic acid than acetic acid is required for pH adjustment.

That which is claimed is:

1. A process for the recovery of a nitrile comprising (1) contacting a product mixture, which comprises a nitrile and hydrogen cyanide, with glycolic acid or a glycolic acid-generating compound to produce a glycolic acid-treated product; and (2) recovering said nitrile from said glycolic acid-treated product.

2. A process according to claim 1 wherein said nitrile is acrylonitrile.

3. A process according to claim 1 wherein the molar ratio of said glycolic acid to said hydrogen cyanide is in the range of from about 0.001:1 to about 1000:1.

4. A process according to claim 2 wherein the molar ratio of said glycolic acid to said hydrogen cyanide is in the range of from about 0.001:1 to about 1000:1.

5. A process according to claim 1 wherein said product mixture is produced by contacting an olefin with ammonia to produce a product mixture comprising acrylonitrile and hydrogen cyanide.

6. A process according to claim 3 wherein said product mixture is produced by contacting an olefin with ammonia to produce a product mixture comprising acrylonitrile and hydrogen cyanide.

7. A process according to claim 2 wherein said product mixture is produced by contacting propylene with ammonia to produce a product mixture comprising acrylonitrile and hydrogen cyanide.

8. A process according to claim 4 wherein said product mixture is produced by contacting propylene with ammonia to produce a product mixture comprising acrylonitrile and hydrogen cyanide.

9. A process according to claim 5 wherein said product mixture is produced by contacting an olefin with ammonia to produce a product mixture comprising acrylonitrile and hydrogen cyanide.

10. A process according to claim 6 wherein said product mixture is produced by contacting propylene with ammonia to produce a product mixture comprising acrylonitrile and hydrogen cyanide.

11. A process according to claim 10 wherein said glycolic acid is present in said product mixture in an amount sufficient to reduce the pH of the said product mixture to below about 4.2.

12. A process comprising (1) contacting an olefin with ammonia to produce a product mixture comprising a nitrile and hydrogen cyanide; (2) contacting said product mixture with glycolic acid or a glycolic acid-generating compound to produce a glycolic acid-treated product; and (2) recovering the nitrile from said glycolic acid-treated product.

13. A process according to claim 12 wherein said nitrile is acrylonitrile.

14. A process according to claim 12 wherein the molar ratio of said glycolic acid to said hydrogen cyanide is in the range of from about 0.001:1 to about 1000:1.

15. A process according to claim 13 wherein the molar ratio of said glycolic acid to said hydrogen cyanide is in the range of from about 0.001:1 to about 1000:1.

16. A process according to claim 12 wherein said olefin is propylene; said nitrile is acrylonitrile.

17. A process comprising (1) contacting propylene with ammonia to produce a product mixture comprising acrylonitrile and hydrogen cyanide; (2) contacting said product mixture with glycolic acid or a glycolic acid-generating compound to produce a glycolic acid-treated product; and (2) recovering the acrylonitrile from said glycolic acid-treated product.

18. A process according to claim 17 wherein the molar ratio of said glycolic acid to said hydrogen cyanide is in the range of from about 0.001:1 to about 1000:1.

19. A process according to claim 17 wherein said glycolic acid is present in said product mixture in an amount sufficient to reduce the pH of the said product mixture to below about 4.2.

* * * * *